United States Patent [19]

Conder et al.

[11] Patent Number: 5,318,896
[45] Date of Patent: Jun. 7, 1994

[54] RECOMBINANT EXPANDASE BIOPROCESS FOR PREPARING 7-AMINODESACETOXY CEPHALOSPORANIC ACID (7-ADCA)

[75] Inventors: Michael J. Conder, Harrisonburg, Va.; Phyllis C. McAda, Woodinville; John A. Rambosek, Seattle, both of Wash.

[73] Assignee: Merck & Co., Inc., Rahway, N.J.

[21] Appl. No.: 933,469

[22] Filed: Aug. 28, 1992

Related U.S. Application Data

[63] Continuation-in-part of Ser. No. 757,879, Sep. 11, 1991, abandoned.

[51] Int. Cl.$^5$ .................. C12P 35/02; C12P 35/06; C12N 9/84
[52] U.S. Cl. ............................ 435/47; 435/51; 435/183; 435/230; 435/935
[58] Field of Search .............. 435/47, 51, 183, 230, 435/243, 254, 320.1, 935; 935/60

[56] References Cited

U.S. PATENT DOCUMENTS 5,070,020 12/1991 Ingolia et al. .................. 435/183
5,108,918 4/1992 Groenen et al. .................. 435/172.3

FOREIGN PATENT DOCUMENTS 0233715 8/1987 European Pat. Off. .
0436355 12/1989 European Pat. Off. .

OTHER PUBLICATIONS

Baldwin et al., "The Enzymatic Ring Expansion of Penicillins to Cephalosporins: Side Chain Specificity", *Tetrahedron*, 43:3009-3014, (1987).

Ballio et al., "Incorporation of $\alpha,\omega$-Dicarboxylic Acids as Side-chains into the Penicillin Molecule", *Nature*, 185:97-99 (1960).

Cantwell et al., "Cloning and Expression of a hybrid *S. clavuligerus* cefE gene . . . ", *Curr. Genet.*, 17:213-221 (1990).

Matsuda et al., "Cloning and Characterization of the Genes . . . ", *J. Bacteriol.*, 169:5815-5820 (1987).

*Primary Examiner*—Keith Baker
*Assistant Examiner*—Stephen Walsh
*Attorney, Agent, or Firm*—John W. Wallen, III; Jack L. Tribble; Paul D. Matukaitis

[57] ABSTRACT

An important intermediate for preparing cephalosporin antibiotics, 7-aminodesacetoxy cephalosporanic acid (7-ADCA), is prepared by a novel bioprocess in which a transformed *Penicillium chrysogenum* strain is cultured in the presence of an adipate feedstock to produce adipoyl-6-APA (6-amino penicillanic acid); and the in situ expression of an expandase gene, e.g., from *Streptomyces clavuligerus*, with which the *P. chrysogenum* has been transformed, converts the adipoly-6-APA by ring expansion to adipoyl-7-ADCA. The final product, 7-ADCA, is then prepared by cleavage of the adipoyl side chain using an adipoyl acylase. The entire synthesis, accordingly, is carried out using bioprocesses, and is efficient and economical.

7 Claims, No Drawings

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

TCTAGACACC ATGG        14

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

GTGAGAGTTG ATGGAC        16

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

TCTAGACACT ATGGAC        16

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

TCTAGACACC ATGGAC 16

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Ser Asn Ser Gly Ala Val Ala Pro Gly Lys Thr Ala Asn Gly Asn Ala
1               5                   10                  15
Leu Leu Leu Gln Asn Pro
            20

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Ser Asn Ser Trp Ala Val Ala Pro Gly Lys Thr Ala Asn Gly Asn Ala
1               5                   10                  15
Leu Leu Leu Gln Asn Pro
            20

( 2 ) INFORMATION FOR SEQ ID NO:7:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Ser Asn Asn Trp Ala Val Ala Pro Gly Arg Thr Ala Thr Gly Arg Pro
1               5                   10                  15
Ile Leu Ala Gly Asp Pro
            20

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGAGAGGATC AGTGAGAGTC CATGGACACG ACGG 34

( 2 ) INFORMATION FOR SEQ ID NO:9:

( i ) SEQUENCE CHARACTERISTICS:
        ( A ) LENGTH: 47 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:9:

ATCTCTTTTC TAATACCTTC ACCATGGGTG AGATTGTACG TGATCCC    47

(2) INFORMATION FOR SEQ ID NO:10:

(i) SEQUENCE CHARACTERISTICS:
(A) LENGTH: 33 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:10:

CGCGGATCCC GGCATCAACG GCTTCGGTCG TAT    33

(2) INFORMATION FOR SEQ ID NO:11:

(i) SEQUENCE CHARACTERISTICS:
(A) LENGTH: 34 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:11:

CGCGGATCCG GGCACGCGCA TGGACATGCC AGTG    34

(2) INFORMATION FOR SEQ ID NO:12:

(i) SEQUENCE CHARACTERISTICS:
(A) LENGTH: 26 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:12:

CAGTAAACGC AACCATGGTT GTCCAG    26

RECOMBINANT EXPANDASE BIOPROCESS FOR PREPARING 7-AMINODESACETOXY CEPHALOSPORANIC ACID (7-ADCA)

This application is a continuation-in-part of application Ser. No. 07/757,879, filed Sep. 11, 1991, now abandoned.

BACKGROUND OF THE INVENTION

1. Field of the Invention

The present invention is in the field of synthesis methods for the preparation of commercial cephalosporin antibiotics, of which there are presently a significant number, these therapeutic agents now being in their fourth generation. The large variety of side chains to be found in commercial cephalosporins and the significant economic importance of the cephalosporins has placed increased importance on achieving more economic and efficient methods of preparing key intermediates which permit ready synthesis of the various cephalosporins.

One of these key intermediates is 7-aminodesacetoxy cephalosporanic acid (7-ADCA), which may be represented by the following formula:

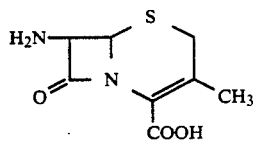

Currently, 7-ADCA is produced from penicillin G and requires four or five chemical steps to expand the penicillin ring system from 5 members to the 6-membered ring which characterizes cephalosporins. As is typical of totally chemical synthesis, this process has serious disadvantages. Among these are the requirements of a multi-step and complex process, expensive reagents, significant quantities of process by-products resulting in effluent treatment problems, and purification of a highly impure starting material before chemical treatment begins. Consequently, there has been an ongoing search for a microbiological or fermentative process which would achieve enzymatic ring expansion and side chain cleavage to provide 7-ADCA on a more economic basis than the chemical process currently in use.

Accordingly, the present invention is particularly in the field of preparing the key cephalosporin intermediate 7-ADCA, and more particularly, in the field of bioprocesses for the preparation of 7-ADCA.

To date, the search for a successful bioprocess for making 7-ADCA has largely proved futile, certainly with respect to one of commercial scale. For example, while it has been possible to prepare 6-amino penicillanic acid (6-APA) by direct fermentation and/or by enzymatic treatment of penicillin G, leaving only ring expansion necessary to give 7-ADCA, it has been found that, unfortunately, the Cephalosporium or Streptomyces enzymes which carry out ring expansion in the normal metabolic pathways of these microorganisms do not accept 6-APA as a substrate. These enzymes, which are collectively referred to in the art as the DAOCS or expandase enzyme, are defined as enzymes which catalyze the expansion of penam ring structures found in penicillin-type molecules to ceph-3-em rings, as found in the cephalosporins. Hereafter, these enzymes will be referred to as "the expandase enzyme".

A substrate on which the expandase enzyme does operate is penicillin N, which upon ring expansion, gives deacetoxy cephalosporin C (DAOC). Here, it is only necessary to cleave the (D)-a-aminoadipoyl side chain to give 7-ADCA, but this side chain has proven stubbornly resistant to enzymatic cleavage, giving only unacceptably low yields.

In accordance with the present invention it has been possible to achieve an efficient bioprocess wherein a penicillin compound (having an adipoyl side chain) is produced by a novel fermentation process in high titers, said penicillin compound being an acceptable substrate for the expandase enzyme system which is produced in situ by the same microorganism which produces the penicillin compound, having been transformed to express said expandase enzyme system. The expandase enzyme then operates to ring expand the penicillin compound to a cephalosporin compound in high yields. And, importantly in the second critical step, the side chain of the penicillin compound, now a cephalosporin compound, is removable by another enzyme system in surprisingly high yields. The unexpected result of this unique bioprocess which comprises the present invention is the production of 7-ADCA in surprisingly high yields.

2. Brief Description of the Prior Art

Cantwell et al., in Curr Genet (1990) 17:213–221, have proposed a bioprocess for preparing 7-ADCA by ring expansion of penicillin V followed by enzymatic hydrolysis of the resulting deacetoxycephalosporin V to form 7-ADCA. This proposal is based on the availability of a cloned penicillin N expandase gene (cefE) from *S. clavuligerus*, Kovacevic et al., *J. Bacteriol.* (1989) 171:754–760 and U.S. Pat. No. 5,070,020. However, since the expandase operates on penicillin N, its natural substrate, but not on penicillin V, the proposal requires genetic engineering to produce a modified expandase gene which can ring-expand the penicillin V. The required modification was not achieved by Cantwell et al., however, and they only succeeded in transforming *Penicillium chrysogenum* with the cef E gene from *Streptomyces clavuligerus* and getting low-level expression of the DAOCS (expandase) enzyme.

The expandase enzyme has been well studied in the art, both with respect to its activity and its genetic sequence. For example, in Wolfe U.S. Pat. Nos. 4,510,246 and 4,536,476, cyclase, epimerase and ring expansion enzymes were isolated separately from a cell free extract of prokaryotic β-lactam producing organisms, including *Streptomyces clavuligerus*, to provide stable enzyme reagents. EP-A-0 366 354 describes an isolated and purified expandase enzyme from *S. clavuligerus* which is characterized, including by a terminal residue and amino acid composition, and is said to have a molecular weight of about 34,600 Daltons. This is in contrast, however, to the molecular weight of 29,000 assigned to what would appear to be the same enzyme in U.S. Pat. No. 4,536,476. EP-A-0 233 715 discloses isolation and endonuclease restriction map characterization of the expandase enzyme obtained from *S. clavuligerus*, transformation and expression in a host of said enzyme, and demonstration of ring expansion of penicillin N substrate using said enzyme. U.S. Pat. No. 5,070,020 discloses the DNA sequence encoding the expandase enzyme obtained from *S. clavuligerus* and describes the transformation of a *P. chrysogenum* strain with an expression vector containing said DNA sequence, thereby obtaining expression of the expandase enzyme. While it is suggested that this enzyme is useful for the expansion of substrates other than penicillin N, there is no actual demonstration of such an expansion.

The work described above has focused on the expandase enzyme derived from prokaryotic *S. clavuligerus*. This same enzyme, or at least an enzyme apparently having the same ring expansion activity, is also expressed by strains of eukaryotic *Cephalosporium acremonium* (also referred to as *Acremonium chrysogenum*). However, in such strains expandase activity is expressed by a bifunctional gene (cefEF), which also expresses the DACS (hydroxylase) activity whose natural function is to convert the desacetoxycephalosporanic acid (DAOC) product of the expandase enzyme to deacetyl cephalosporin C (DAC). The result is a single, but bifunctional expandase/hydroxylase enzyme. While there have been efforts to separate the activities of these two gene products, none have yet been successful. For example, EP-A-0 281 391 discloses the isolation and DNA sequence identification of the DAOCS/DACS gene obtained from *C. acremonium* ATCC 11550 together with the corresponding amino acid sequences of the enzymes. A *Penicillium* is transformed and expresses the enzymes, however, the attempted conversion of penicillins G and V to the corresponding cephalosporins is never demonstrated. Further, despite a suggestion that genetic engineering techniques provide a ready means to separate the genetic information encoding DAOCS from DACS and separately express them, no actual demonstration of such separation is set forth.

The DAOCS/DACS (expandase/hydroxylase) enzyme of *C. acremonium* has also been well studied in the art, both with respect to its activity and its characteristics and genetic sequence. For example, in Demain U.S. Pat. No. 4,178,210; 4,248,966; and 4,307,192 various penicillin-type starting materials are treated with a cell-free extract of *C. acremonium* which epimerizes and expands the ring to give a cephalosporin antibiotic product. Wu-Kuang Yeh U.S. Pat. No. 4,753,881 describes the *C. acremonium* enzyme in terms of its isoelectric point, molecular weights, amino acid residues, ratio of hydroxylase to expandase activities and peptide fragments.

The prior art discussed above deals with only a single aspect of the present invention, i.e., the transformation of a *P. chrysogenum* strain with the gene expressing the expandase enzyme and obtaining expression of that enzyme. The art, however, has only used the expressed enzyme to ring-expand penicillin N, not penicillins G and V. Even in that case, penicillin N has a 7-position side chain which cannot be cleaved enzymatically to give 7-ADCA, as in the method of the present invention. The present invention relies on the surprising discovery that an adipoyl side chain can be efficiently added by a *P. chrysogenum* strain, that the expandase enzyme expressed in situ can use that compound efficiently as a substrate for ring expansion to adipoyl 7-ADCA, and that the adipoyl side chain can then be efficiently removed by yet another enzyme to give 7-ADCA. While various isolated fragments of the present invention may be found in the prior art, there has been no suggestion that they be combined to give the unexpected results obtained with the method of the present invention.

For example, production of 6-adipoyl penicillanic acid is known in the art; see Ballio, A. et al., *Nature* (1960) 185, 97–99. The enzymatic expansion of 6-adipoyl penicillanic acid on an in vitro basis is also known in the art. See Baldwin et al., *Tetrahedron* (1987) 43, 3009–3014; and EP-A-0 268 343. And, enzymatic cleavage of adipoyl side chains is also known in the art; see Matsuda et al., *J. Bact.* (1987) 169, 5815–5820.

The adipoyl side chain has the following structure: $COOH-(CH_2)_4-CO-$, while a side chain of closely related structure is that of glutaryl, having the following formula: $COOH-(CH_2)_3-CO-$. The enzymatic cleavage of glutaryl side chains is known in the art. See, e.g., Shibuya et al., *Agric. Biol. Chem.* (1981) 45, 1561–1567; Matsuda and Komatsu, *J. Bact.* (1985) 163, 1222–1228; Matsuda et al., *J. Bact.* (1987) 169, 5815–5820; Jap. 53-086084 (1978-Banyu Pharmaceutical Co. Ltd.); and Jap. 52-128293 (1977-Banyu Pharmaceutical Co. Ltd.).

Also, EPA-A-0 453 048 describes methods for improving the adipoyl-cleaving activity of the glutaryl acylase produced by Pseudomonas SY-77-1. By substituting different amino acids at certain locations within the alpha-subunit, a three to five times higher rate of adipoyl cleavage (from adipoyl-serine) was observed. It should be noted that although EP-A-0 453 048, apparently, demonstrates an acylase with improved activity towards adipoyl-side chains, it does not describe any ways (either chemical or through a bioprocess in any way analogous to that described in the instant specification) in which an adipoly-cephalosporin might be generated in the first place.

Where a (D)-a-aminoadipoyl side chain is present, it is known in the art to first enzymatically remove the amino group and shorten the side chain with a (D)-aminoacidoxidase, leaving a glutaryl (GL-7) side chain, with removal of the glutaryl side chain by a second enzyme (glutaryl acylase). Such a two-step cleavage is disclosed in Matsuda U.S. Pat. No. 3,960,662; EP-A-0 275 901; Jap. 61-218057 (1988-Komatsu, Asahi Chemical Industry Co.); WO 90/12110 (1990-Wong, Biopure Corp.); and Isogai et al., *Bio/Technology* (1991) 9, 188–191.

REFERENCE TO COPENDING APPLICATION

Reference is made to copending application Ser. No. 07/953,492, filed Oct. 6, 1992, which discloses a bioprocess for making 7-ACA that relies on expression of the activity of the expandase enzyme in a *P. chrysogenum* transformant in the same manner as the bioprocess for making 7-ADCA described herein. However, in the 7-ACA bioprocess, additional transformations are required for the expression of additional enzymatic activities, in order to achieve a wholly different recombinant metabolic pathway to a distinct final product, none of which is suggested in the instant specification.

In order to facilitate a better understanding of the method of the present invention and the teachings of the prior art references discussed above, set out immediately below is a representation of the various stages in the metabolic pathways leading to penicillin G and cephalosporin C, the intermediate products, and the enzymes which carry out the transformations involved.

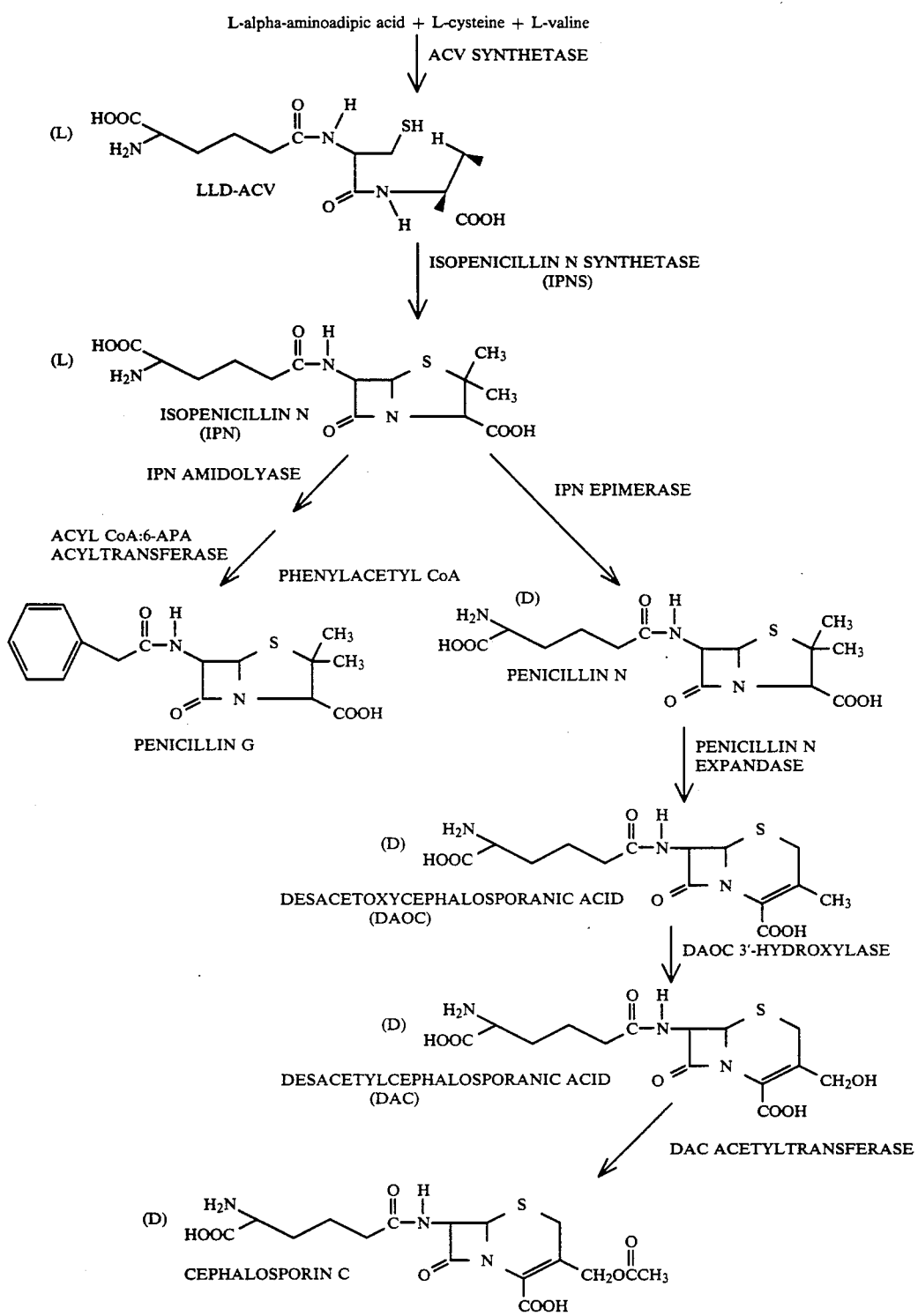

SUMMARY OF THE INVENTION

The present invention relates to a novel bioprocess for preparing 7-aminodesacetoxy cephalosporanic acid (7-ADCA) comprising the steps of 1) maintaining in a culture medium capable of sustaining its growth, a strain of *Penicillium chrysogenum* which produces isopenicillin N and adding to said culture medium an adipate feedstock comprising adipic acid, or one or more of its salts and esters which are capable of being assimilated and utilized by said strain of *Penicillium chrysogenum* to produce adipoyl-6-amino penicillanic acid (adipoyl-6-APA), whereby said adipoyl-6-APA is produced;

wherein said strain of *Penicillium chrysogenum* has been transformed by DNA encoding the activity of the expandase enzyme capable of accepting said adipoyl-6-APA as a substrate, whereupon as a result of its expression, said adipoyl-6-APA produced by said strain is also thereafter in situ ring-expanded to form adipoyl-7-ADCA; and 2) contacting said adipoyl-7-ADCA with an adipoyl acylase whereby the adipoyl side chain is removed and the 7-ADCA product is formed; and said product is then isolated.

As used herein, the following terms have the indicated meanings:

"adipoyl-6-APA" means [2S-(2α,5α,6β)]-3,3-dimethyl-7-oxo-6-[(hexane-1,6-dioyl)amino]-4-thia-1-azabicyclo-[3.2.0]heptane-2-carboxylic acid; and "adipoyl-7-ADCA" means 7-[(hexane-1,6-dioyl)amino]-3-methyl-8-oxo-5-thia-1-azabicyclo-(4.2.0)-oct-2-ene-2-carboxylic acid.

In particular, the present invention relates to the novel bioprocess for preparing 7-aminodesacetoxy cephalosporanic acid (7-ADCA) recited above in which the adipate feedstock is disodium adipate, in which the DNA encoding the activity of the expandase enzyme is derived from Streptomyces clavuligerus ATCC 27064, and in which the adipoyl acylase is derived from Pseudomonas species.

The present invention further relates to a recombinant DNA expression vector comprising the DNA encoding the activity of the expandase enzyme derived from Streptomyces clavuligerus ATCC 27064, and a promoter which drives expression of said expandase activity-encoding DNA comprising plasmid pPenFTSO, as hereinafter described.

The present invention further relates to a Penicillium chrysogenum host cell transformed with a recombinant DNA expression vector comprising the DNA encoding the activity of the expandase enzyme derived from Streptomyces clavuligerus ATCC 27064, and a promoter which drives expression of said expandase activity-encoding DNA comprising the promoter of the Penicillium chrysogenum IPNS gene. In particular, the present invention relates to a Penicillium chrysogenum host cell transformed with a recombinant DNA expression vector comprising plasmid pPenFTSO, as hereinafter described.

The present invention still further relates to a method comprising the step of culturing a recombinant Penicillium chrysogenum host cell under conditions suitable for gene expression, wherein said recombinant host cell comprises a recombinant DNA expression vector comprising the DNA encoding the activity of the expandase enzyme derived from Streptomyces clavuligerus ATCC 27064, and a promoter which drives expression of said expandase activity-encoding DNA comprising the promoter of the Penicillium chrysogenum IPNS gene. In particular, the present invention relates to a method of culturing a recombinant Penicillium chrysogenum host cell under conditions suitable for gene expression, wherein said recombinant host cell comprises a recombinant DNA expression vector comprising plasmid pPenFTSO, as hereinafter described.

DETAILED DESCRIPTION OF THE INVENTION

The primary aspect of the present invention is a novel bioprocess for preparing 7-aminodesacetoxy cephalosporanic acid (7-ADCA), a key intermediate in the preparation of synthetic commercial cephalosporins, which may be represented by the following structural formula:

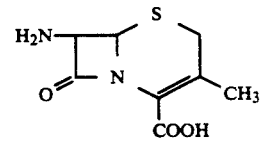

In addition to the cephalosporin nucleus, the distinctive features of 7-ADCA are the 7-amino group and the 3-methyl group. The 7-amino group is one which may be converted to any number of derivative side chains, and thus forms the basis for synthesizing various commercial cephalosporins. The 3-methyl group will usually, but not always, as in the case of cephalexin, have to be converted to some other side chain to synthesize a commercial cephalosporin.

The 7-ADCA product of the method of the present invention may be contrasted with cephalosporin C, another key cephalosporin intermediate which may be represented by the following structural formula:

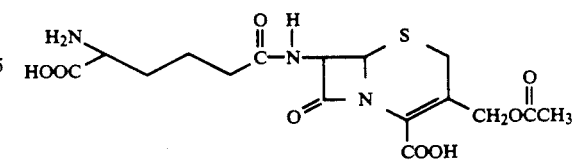

For this intermediate, the 3-acetyloxymethyl side chain may be acceptable for commercial cephalosporins. However, the 7-(D)-α-aminoadipoyl side chain is not acceptable for further synthetic derivation, and must be cleaved to give the acceptable 7-amino group. Unfortunately, the 7-(D)-α-aminoadipoyl side chain has always proven difficult to remove, whether by chemical or biochemical means.

Definitions

As used in the instant specification, and particularly in the section entitled Description of Preferred Embodiments, the following terms have the indicated meanings:

| | |
|---|---|
| 7-ADCA | 7-Aminodesacetoxycephalosporanic acid |
| 6-APA | 6-Aminopenicillanic acid |
| DAOC | Desacetoxycephalosporanic acid |
| DAOCS | DAOC synthetase |
| DAC | Deacetylcephalosporin C |
| DACS | DAC synthase |
| IPNS | Isopenicillin N synthetase |
| Tris | Tris[hydroxymethyl]aminomethane |
| EDTA | Ethylenediaminetetraacetic acid |
| DEPC | Diethylpyrocarbonate |
| TE | Tris/EDTA buffer |
| SSC | Salt (Sodium chloride), sodium citrate buffer |
| SDS | Sodium dodecylsulfate |
| PEG | Polyethylene glycol |

Penicillium chrysogenum Culture

The first step of the method of the present invention comprises the step of maintaining in a culture medium capable of sustaining its growth, a strain of Penicillium chrysogenum which produces isopenicillin N and adding to said culture medium an adipate feedstock comprising adipic acid, or its salts and esters. The adipate feedstock may be added to the culture medium after inoculation with *P. chrysogenum*, but it is preferred that it already be present in the culture medium at the time that inoculation takes place. The adipic acid, or its salts and esters are such that they are capable of being assimilated and utilized by said strain of *P. chrysogenum* to produce adipoyl-6-APA; wherein said strain of *P. chrysogenum* has been transformed by DNA encoding the activity of the expandase enzyme, whereupon as a result of its expression, said adipoyl-6-APA is in situ ring-expanded to form adipoyl-7-ADCA.

Other species of the genus Penicillium besides the chrysogenum species produce isopenicillin N. However, historically the highest producing strains of isopenicillin N have all been developed by well-known techniques of strain improvement from the chrysogenum species. As a practical matter, then, the present invention has been limited to strains of *Penicillium chrysogenum*, although its applicability to other species is obvious. Any deposited strain of *Penicillium chrysogenum* or other publicly available source of such strain is a suitable starting point for carrying out the method of the present invention.

The culture medium capable of sustaining the growth of a strain of *Penicillium chrysogenum* which produces isopenicillin N is of the type with which the person of ordinary skill in the art would be readily familiar. For example, the culturing would be carried out by the submerged aerobic fermentation method, and the medium employed would be selected from a number of suitable media available. Typical media utilize carbon sources such as sucrose, glucose, and starch; nitrogen sources such as soybean meal and grits, cotton seed oil, peanut meal, and various amino acids, mixtures thereof, and peptones. Production requirements emphasize yield and ease of isolation, and thus preferred media for such situations may be molasses as the carbon source and soybean meal and amino acids as the nitrogen source.

Nutrient inorganic salts are commonly added to the culture medium, and include salts capable of supplying the following ionic components: sodium, potassium, ammonium, calcium, phosphate, sulfate, chloride, bromide, nitrate, carbonate, ferric, ferrous, magnesium, manganese, etc. Trace elements are also usually essential for the growth, development and metabolism of the *Penicillium chrysogenum*, and can be added directly to the culture medium unless supplied already as contaminants, essentially, of the other culture medium ingredients.

The *Penicillium chrysogenum* strains can be cultured in equipment of small volume such as 1 L shake flasks where it is desired to produce only small quantities of 7-ADCA. Where larger quantities of the adipoyl-7-ADCA are desired, however, large scale fermentation tanks under submerged aerobic fermentation conditions will be employed.

In carrying out the large scale preparation of adipoyl-7-ADCA, spores of the *Penicillium chrysogenum* strain are maintained on an agar slant. The spores from the slant are employed to inoculate a vegetative medium having a small volume. The vegetative medium is incubated to produce a heavy, fresh, actively growing culture of the microorganism. This vegetative growth is then employed as the inoculum for the large scale fermentation medium. In certain instances it may be desirable to include yet a further vegetative medium as the inoculum for the fermentation medium. Such second stage vegetative media are commonly employed when the volume of the fermentation medium is significantly larger than the first vegetative medium. In this manner, the spores of the microorganism are cultured at first in a small volume of vegetative medium to obtain inoculum for a vegetative medium of larger volume. The larger volume vegetative medium then supplies sufficient concentration of the microorganism to initiate a rapid onset of the fermentation in the large scale fermentation tank. The vegetative medium can have the same composition as the fermentation medium or it can contain additional ingredients to spur the growth and development of the microorganism on a small scale.

The *Penicillium chrysogenum* strains employed in the method of the present invention are most effectively cultured at temperatures between about 20° and 30° C., but optimal yields will be obtained when the temperature is between about 22° and 28° C., preferably about 25° C.

Maximum production of adipoyl-7-ADCA occurs when the *Penicillium chrysogenum* strain is cultured in large scale tanks for a period of between about 10 and 30 days, preferably 15 to 25 days. However, when cultured in small scale apparatus, such as 250 mL shake flasks, the growth of the microorganism is more rapid and it produces adipoyl-7-ADCA in a shorter time, e.g., 4 to 15 days, frequently 5 to 7 days.

If the terminal pH in large scale fermentation tanks reaches 8.0 or higher, yield of adipoyl-7-ADCA may be adversely affected. In such situations, it is desirable to monitor the pH of the culture medium throughout the fermentation. If it appears that the pH will reach such levels prior to the time of maximum production of adipoyl-7-ADCA occurs, the pH can be conveniently adjusted downward by adding a suitable acid or buffering agent to the fermentation medium.

The production of adipoyl-7-ADCA can be followed by testing samples of the fermentation broth chromatographically.

As with most submerged aerobic fermentations, sterile air is passed through the culture medium to obtain more efficient growth of the *Penicillium chrysogenum* strain and increased production of adipoyl-7-ADCA. The volume of air forced through the culture medium is usually at least approximately 0.2 volumes of air per minute per volume of culture medium. However, an increased rate of air passage can often have a beneficial effect on the production of adipoyl-7-ADCA.

The *Penicillium chrysogenum* strain will typically produce, in addition to adipoyl-7-ADCA, many side products and metabolites. Since some of these are acid labile, it is desirable in the recovery of adipoyl-7-ADCA from the fermentation medium, to treat the whole fermentation broth at an acid pH for a short time in order to destroy some of the co-produced impurities. The adipoyl-7-ADCA fermentation product is recovered from the filtered fermentation broth thus treated and optionally may be separated from the other components of the fermentation medium by chromatography over an ion exchange resin and may be further purified by chromatography if necessary before the subsequent step of enzymatic cleavage of the adipoyl side chain. It is also possible to carry out such ion exchange chromatography separation after side chain cleavage has been carried out. One of the major side products which presents separation problems is adipoyl-6-APA, and it is possible to chemically or enzymatically degrade this side product in order to make separation more facile. Initially, the filtered fermentation broth is subjected to a preliminary purification procedure which can include an initial extraction with a water immiscible organic solvent, such as n-butanol or amyl acetate, to remove impurities. The extracted broth can then be further purified in a preliminary manner by chromatography over activated carbon.

Addition of Adipate Feedstock

Preferably, at the time the fermentation culture for the *Penicillium chrysogenum* is established as described above, i.e., prior to inoculation, an adipate feedstock is added to the other ingredients of the fermentation culture medium. Optionally, the adipate feedstock may be added at some time after inoculation, e.g., at 1, 2 and/or 3 days after inoculation. The adipate feedstock is defined as adipic acid, or any one or more salts or esters of adipic acid which are capable of being assimilated and utilized by the strain of *Penicillium chrysogenum* being cultured to produce adipoyl-6-APA. The adipic acid, salts and esters may be used alone or in any combination. The disodium salt is preferred, although potassium and mixed salts with sodium would also be suitable. The methyl ester could be used, but the ethyl ester is water insoluble. The adipic acid salt or ester must be such that it can be assimilated and utilized by the strain of *Penicillium chrysogenum* to make adipoyl-6-APA. For example, adipic acid itself might be suitable, even though it is water insoluble, if under proper pH conditions an assimilatable salt is formed.

Suitable Expandase Enzymes

The strain of *Penicillium chrysogenum* which has been cultured and provided with an adipate feedstock as described above so that it produces adipoyl-6-APA, is also one which has been transformed by DNA encoding the activity of the expandase enzyme, whereupon as a result of its expression, said adipoyl-6-APA is in situ ring-expanded to form adipoyl-7-ADCA.

The adipoyl-6-APA is produced intracellularly by the adipate feedstock cultured *Penicillium chrysogenum*. In that intracellular setting, i.e., on an in situ basis, the transformed *Penicillium chrysogenum* also expresses DNA encoding the activity of the expandase enzyme, whereupon the enzyme operates on the adipoyl-6-APA as a substrate, and ring-expands it to form adipoyl-7-ADCA.

The novel bioprocess of the present invention includes within its scope the transformation of a *Penicillium chrysogenum* strain of the type described above with any DNA encoding the activity of the expandase enzyme, whereupon as a result of its expression, adipoyl-6-APA is in situ ring-expanded to form adipoyl-7-ADCA. Thus, the DNA with which the *Penicillium chrysogenum* is transformed must express an enzyme having not only the activity of the expandase enzyme as understood in the art, i.e., the ability to ring-expand isopenicillin N to DAOC, but the ability to ring-expand adipoyl-6-APA to adipoyl-7-ADCA. However, it is contemplated, based on side chain similarity, that any expandase enzyme will be operable in the novel bioprocess of the present invention.

It has already been noted under the section describing the prior art, that the expandase enzyme derived from *Streptomyces clavuligerus* ATCC 27064 has been fully sequenced as well as characterized by endonuclease restriction mapping. However, what would appear to be the same enzyme, derived from *S. clavuligerus* NRRL 3585, has been reported to have a different molecular weight, but it has not been sequenced.

These expandase enzymes already identified in the prior art are useful in the novel bioprocess of the present invention. Other expandase enzymes not yet identified, derived from different strains of *S. clavuligerus*, or even from microorganisms of different genera, may also prove to be suitable for carrying out the novel bioprocess of the present invention. The procedures for identifying such new strains and genera of useful microorganisms and for isolating the putative expandase enzymes and establishing that they are suitable for use in the method of the present invention, are straightforward and well within the skill of the artisan. Screening of cell-free extracts of candidate new strains and genera of useful microorganisms may be done in a reliable and reproducible manner by adding said extracts to the adipoyl-6-APA substrate in the presence of known DAOCS co-factors which include ferrous ($Fe^{2+}$) ions, ascorbate, a-ketoglutarate and adenosine triphosphate (ATP). The adipoyl-6-APA substrate may be prepared in sufficient quantities by feeding an adipate feedstock to an untransformed *Penicillium chrysogenum* in a manner analogous to that described in detail further below. The desired expandase enzyme is present if adipoyl-7-ADCA is formed, the presence of which may be detected by chromatography.

It is also possible, using well-known recombinant techniques, to generate DNA probes, based on the expandase sequence of *S. clavuligerus* and *C. acremonium*, for example, to screen the DNA contents of a candidate microorganism likely to produce an expandase suitable for use in the method of the present invention.

Potential Sources for Expandase Enzymes

Expandase enzymes, as already noted, are enzymes which catalyze the expansion of penam ring structures (found in penicillin-type molecules) to ceph-3-em rings (as found in the cephalosporins). Any organism producing metabolites which contain a cephem ring is, therefore, a potential source for an expandase-encoding DNA. Examples of such organisms are listed below, but this list is exemplary only and should not be considered exhaustive:

Fungi
*Cephalosporium acremonium*
*Cephalosporium sp.*
*Emericellopsis*
*Paecilomyces*
*Scopulariopsis*
*Diheterospora*
*Spiroidium*
*Anoxiopsis*
    Actinomycetes
*Streptomyces clavuligerus*
*S. lipmanii*
*S. wadayamensis*
*S. todorominensis*
*S. filipinensis cephamycini*
*S. heteromorphus*
*S. panayensis*
*S. griseus*
*S. cattleya*
*Nocardia lactamdurans*
    Other bacteria
*Flavobacterium sp.*
*Alcaligenes denitrificans*
*Mycoplana bullata*
*Providencia rettgeri*
*Lysobacter lactamgenus*

The expandases of the organisms listed above are merely candidates for further investigation, and it may be that not all of them will be suitable for the novel process of the present invention. For example, use of those enzymes which possess both expandase and hydroxylase activities, such as that from C. acremonium, might result in the synthesis of hydroxylated adipoyl-7-ADCA, i.e., DAC with an adipoyl side chain.

Isolating DNA Fragments Encoding Expandase Activity

Once the presence of a desired expandase enzyme has been detected in the manner described above, procedures for the isolation of the DNA encoding the expandase enzyme activity are also straightforward and well known in the art. DNA probes based on the known sequences and partial sequences of the genes encoding the expandase enzymes are constructed which will hybridize to the desired enzyme-encoding DNA to be isolated. The construction of such probes is based on a knowledge of the amino acid and nucleotide base-sequence encoding the expandase enzyme, as well as the codon preferences of the particular microorganism involved. A detailed description of typical procedures of this type applied to the genomic DNA of *Streptomyces clavuligerus* ATCC 27064 is set out further below.

Isolation of the DNA encoding the expandase enzyme activity is accomplished using the restriction and ligation procedures well known in recombinant DNA technology. It is necessary to have an endonuclease restriction map of the genome of the microorganism involved, so that the proper restriction fragment can be produced and isolated. Restriction maps for *S. clavuligerus* and *C. acremonium* are already available; thus, for the former, restriction enzymes Bam HI and Sal I are used and electrophoresis provides the desired 1.8 to 2.2 kb sized fragments.

Transformation of the Penicillium chrysogenum Strain

Once the DNA fragments encoding the expandase activity are obtained, they may be inserted (ligated) into a plasmid or other expression vector, along with DNA fragments comprising promoters, translational activating sequences, resistance markers, regulatory sequences, cosmid formers, and any other DNA sequences which permit or promote transformation, drive expression of the gene product, and facilitate isolation of the transformants. The expression vector which has thus been constructed is then used to achieve transformation of the *Penicillium chrysogenum* strain and intracellular expression of the activity of the expandase enzyme. The techniques used to achieve transformation and expression are well known in the art, and a detailed description of such typical procedures is set out further below.

As already detailed further above, the transformed *Penicillium chrysogenum* strain expresses the activity of the expandase enzyme intracellularly, which then operates in situ on the adipoyl-6-APA substrate to ring-expand it to adipoyl-7-ADCA.

Novel Transformant

The specific *Penicillium chrysogenum* transformant expressing the activity of the expandase gene which is a preferred embodiment of the present invention is novel with respect to such constructions in the prior art as that in Cantwell et al. (1990) *Current Genetic*, 17, 213-221. In both constructions, in vitro mutagenesis is used to connect the promoter to the expandase gene. In the Cantwell construction, manipulation introduces a NdeI site at the ATG of the expandase gene which is ligated to the XbaI site at the 3' end of the INPS promoter by a XbaI/NdeI linker. In the construction of the present invention, an NcoI site is created at the ATG of the expandase gene and ligated to the NcoI site at the 3' end of the IPNS linker. This creates the following sequences around the promoter-gene junctions in these constructions:

|  |  | XbaI | NcoI |  |
|---|---|---|---|---|
| IPNS promoter | 5' | TCT AGAC | ACC ATGG | 3' SEQ ID NO:1 |
| Strep expandase | 5' | GTGAGAG | TTGATGGAC | 3' SEQ ID NO:2 |
| Cantwell | 5' | TCT AGAC | ACT ATGGAC | 3' SEQ ID NO:3 |
| Present Invention | 5' | TCT AGAC | ACC ATGGAC | 3' SEQ ID NO:4 |

The Cantwell construction replaces a C with a T, whereas, in the construct of the present invention the C is retained; thus the sequence of the IPNS promotor immediately adjacent to the ATG start codon exactly matches that which is found with the naturally occurring IPNS gene. It is possible that the promoter of the prior art, although differing by only a single nucleotide base, may lead to a lower efficiency of translation efficiency, and consequently to a lower level of expandase gene expression.

Other differences are in the regions of the promotor or gene included in the constructions. The Cantwell construction contains the 5'BamHI to XbaI 3' region of the IPNS promoter, whereas, the vector of the present invention contains the 5' NcoI to NcoI 3' region of the promotor [Diez, et al., (1990), *J. Biol. Chem.* 265, 16358-16365]. This results in approximately 250 bps additional on the 5' end of the IPNS promoter in the Cantwell construction. However, this region is in the open reading frame of the ACV synthetase gene upstream of the IPNS gene.

The Cantwell construction also contains the Streptomyces gene from the ATG to the BamHI site 3' of the gene, whereas the vector of the present invention contains the ATG to the SalI site 3' of the gene [Kovacevic et al. (1989), *J. Bacteriol.*, 171, 754-760]. This results in approximately 1000 bps of additional 3' end sequence on the Cantwell construction. The construction of the present invention still contains the upstream region of the expandase gene to the BamHI site 5' of the ATG; however, it is separated from the reading frame of the expandase gene by the IPNS promotor.

Another difference of the construct of the present invention over that described in the prior art relates to the selectable marker which is used. The use of a Penicillium IPNS promoter: phleomycin gene fusion in the construct of the present invention tends to select for integration of multiple copies or integration at loci that allow high level expression, and thus potentially may give a higher percentage of transformants that express the expandase gene at high level.

A novel transformant of the type described above, comprising a *Penicillium chryosgenum* host cell transformed with the recombinant DNA expression vector, plasmid pPenFTSO integrated into the chromosomal DNA of said host cell, and identified as PC100, has been deposited with the American Type Culture Collection (ATCC), 12301 Parklawn Drive, Rockville, Md. 20852, under the accession number ATCC 74182 (date of deposit: Aug. 27, 1992).

Cleavage of the Adipoyl Side Chain

The next step in the novel bioprocess of the present invention is the cleavage of the adipoyl side chain from the adipoyl-7-ADCA, which requires treatment of the product of the preceding step with an adipoyl acylase enzyme system. As already noted above, one of the significant achievements of the present invention is the ability to carry out all of the steps leading up to formation of the adipoyl-7-ADCA in a single fermentation culture. This achievement provides exceptionally improved efficiency in not having to isolate and partially purify intermediate products from step to step of the process. In this last step, however, the adipoyl acylase enzyme system is not present, i.e., has not been generated in situ in the original fermentation culture.

If the novel bioprocess of the present invention is being carried out in a batch-wise manner, then it will be necessary to isolate and partially purify the product of the first step, and preliminary procedures for doing this have already been described above.

Nevertheless, the process of the present invention may be carried out in any way which effectively brings the adipoyl acylase into contact with the adipoyl-7-ADCA so that enzymatic conversion of that compound to 7-ADCA can take place. This is the definition of the term "contacting" in its broadest context. It is possible to employ a cell free broth of crude adipoyl-7-ADCA as the feed stream and treat it in a batch-wise fashion with crude adipoyl acylase broth. This approach realizes some efficiencies since it does not require any substantial purification of the reactants initially. Of course, modifications are possible. E.g., the reactants may be purified to whatever extent desired before being brought into contact with each other. Also, it would be possible to carry out the process in a continuous manner rather than batch-wise. The contacting of the reactants themselves may be modified in various ways in keeping with advances in process technology. Thus, an immobilized enzyme may be used, e.g., in the form of a column containing the adipoyl acylase with the adipoyl-7-ADCA being passed through the column. The immobilized enzyme may also be added to the adipoyl-7-ADCA solution as a suspension. Such immobilized enzyme systems offer the advantages of easy enzyme recovery and multiple reuse. Another example of such process technology is that relating to membrane reactors. The preferred method of contacting the reactants is by way of the immobilized enzyme column.

Adipoyl Acylase Enzymes Useful in the Cleavage Step

There are a number of enzymes with known specificity towards adipoyl side chains. Results obtained with an adipoyl acylase commercially available from the RAEV Corp. are detailed in the working examples further below. Seven other enzymes have been reported in the literature which remove adipoyl side chains from cephalosporin-type molecules. Six of these seven enzymes are from Pseudomonas species, and the seventh is from a Bacillus species. Some similarities exist between certain of the Pseudomonad enzymes, but all seven differ to some extent in their physical/biological properties. Some of their characteristics are summarized below:

| ENZYME (Pseudomonas and Bacillus strains) | REFERENCE | APPROX. MOL. WT. (Subunit) |
|---|---|---|
| P. SY 77-1 (Toyo Jozo) | Shibuya, et. al (1981) | Apparently same as GK 16 below |
| P. GK16 (Asahi) | Matsuda, Komatsu (1985) | 16,000 54,000 |
| P. SE83 (acyI) (Asahi) | Matsuda, et al. (1987) | 38,200 19,900 |
| P. SE83 (acyII) (Asahi) | Matsuda, et al. (1987) | 25,400 58,200 |
| P. diminuta N176 (Fujisawa) | Aramori, et al (1991a)* | 58,000 26,000 |
| P. diminuta V22 (Fujisawa) | Aramori, et al. (1991a)* | ? ? |
| Bacillus laterosporus J1 | Aramori, et al. (1991b)** | 70,000 (monomeric) |
| Pseudomas sp. (RAEV Corp.) | — | 16,000 54,000 |

\* Aramori et al., J. Ferment. Bioeng. (1991) 72: 232-243.
\*\* Aramori et al., J. Bacteriol. (1991) 173: 7848-7855.

All of the above adipoyl acylase enzymes are useful in the novel bioprocess of the present invention. Other adipoyl acylases useful in the method of the present invention may be readily discovered by testing the candidate enzyme against adipoyl-7-ADCA, the actual substrate upon which it must operate. A positive result gives a reliable and reproducible method of determining that a candidate enzyme is indeed useful in the method of the present invention. The substrate can be prepared in a straightforward manner from the reaction of adipic anhydride with 7-ADCA using a modification of the procedure reported by Szewczuk and Wellman-Bednawska in Clin. Chim. Acta (1978) 84, 19-26. The adipic anhydride may be prepared in accordance with the method of Albertson and Lundmark described in J. Macromol. Sci. Chem. (1990) A27, 397-412. The 7-ADCA is available from several commercial sources, including E. R. Squibb & Sons, Ltd., New Jersey, and Interchem Corp., New Jersey.

If it is desired to carry out a rough screening of candidate enzymes using a rapid colorimetric method, one may substitute for the adipoyl-7-ADCA substrate a colorimetric substrate such as adipoyl-PABA (para-aminobenzoic acid) or adipoyl-PNA (para-nitroaniline). Cleavage of the side chain gives a color generating species whose presence and concentration is readily determined using a colorimeter. For more detailed information concerning these and other suitable colorimetric methods, see Marelli, L. P. (1968) J. Pharm. Sci. 57: 2172-2173; Szasz, G. (1969) Clin. Chem. 15: 124-136; Szewczuk, A. et al. (1980) Anal. Biochem. 103: 166-169; and Reyes, F. et al. (1989) J. Pharma. Pharmacol. 41: 136-137.

A comparison was made of the N-terminal amino-acid sequences of the RAEV enzyme with the large subunits of acyII and the GK16 enzymes set out in the table above. The results of the comparison are shown below (where parentheses indicate less than conclusive assignments):

RAEV - SEQ ID NO:5
    S N (S) (G) A V A P G K T A N G N A L (L) L Q N (P)
GK16 - SEQ ID NO:6
    S N S W A V A P G K T A N G N A L L L Q N P
acyII - SEQ ID NO:7
    S N N W A V A P G R T A T G R P I L A G D P From the sequences shown, it is apparent that all three of these peptides are related. However, a protein having an N-terminal sequence similar to those shown above will not necessarily possess adipoyl acylase activity, as is the case with a penicillin G acylase produced by a strain of Arthrobacter. On the other hand, there are adipoyl acylases useful in the method of the present invention which do not exhibit significant homology to the above N-terminal sequence. For example, the Asahi enzyme acyI and the Fujisawa *B. laterosporus* J1 acylase set out in the table further above, which have been shown to have some adipoyl-7-ACA acylase activity, do not share any sequence homology with the other enzymes set out above. Consequently, the scope of the present invention with respect to the adipoyl acylases useful in the second step of the novel bioprocess is determined by whether or not a candidate enzyme is able to cleave the adipoyl side chain from adipoyl-7-ADCA, a matter which may be determined readily and reliably, as detailed above.

Other approaches to finding suitable adipoyl acylases are possible. For example, EPA-A-0 453 048 describes methods for improving the adipoyl-cleaving activity of the glutaryl acylase produced by Pseudomonas SY-77-1. By substituting different amino acids at certain locations within the alpha-subunit, a three to five times higher rate of adipoyl cleavage (from adipoyl-serine) was observed. Such improved enzymes would also be suitable for use in the present invention. It should be noted that although EP-A-0 453 048, apparently, demonstrates an acylase with improved activity towards adipoyl-side chains, it does not describe any ways (either chemical or through a bioprocess in any way analogous to that described in the instant specification) in which an adipoyl-cephalosporin might be generated in the first place.

DESCRIPTION OF PREFERRED EMBODIMENTS

There follows a detailed description of certain preferred embodiments of the present invention, but these are intended to be illustrative only, and not in any way a limitation of the present invention.

EXAMPLE 1

*Penicillium chrysogenum* Culture Conditions

The *Penicillium chrysogenum* strain used in these procedures was maintained on plates containing LCSB medium composed of lactose, monohydrated, 1.5% (w/v); corn steep liquor, 0.5% (v/v); peptone, 0.05% (w/v); NaCl, 0.4% (w/v); $MgSO_4$-7 $H_2O$, 0.05% (w/v); $KH_2PO_4$, 0.06% (w/v); $FeCl_3$-6 $H_2O$, 0.0005% (w/v); $CuSO_4$-5 $H_2O$, 0.0002% (w/v); agar, 3.0% (w/v); in one liter of distilled water, pH 4.8. After 12 days at 25° C. and 65% relative humidity, single colonies were removed and added to 2 mL of sterilized water in a screw-top tube containing glass beads. After macerating the culture growth by vortexing, the suspension was used to inoculate rice flasks. The rice flasks contained 25 g/250 mL flask of Uncle Ben's converted rice, natural long grain, which has been washed with three to four volumes of distilled water for seven minutes, mixed every 30 seconds, and then drained until the water uptake into the rice was approximately 25%. After 12 days at 25° C. and 65% humidity, the spores were washed from the rice with 50 mL of sterile water. The spore suspension was used to inoculate liquid cultures and also to provide lyophiles of the cultures for storage at 4° C. The spores were added to an equal volume of 5% skim milk and lyophilized in sterile ampoules.

A two-stage fermentation of the strain in shake-flasks was used for the production of penicillins or for the production of mycelia as a source of RNA or DNA. The seed stage was initiated by adding $1 \times 10^8$ spores to 50 mL/500 mL flask of medium composed of glucose, 3.0% (w/v); pharmamedia, 1.0% (w/v); corn steep liquor, 3.0% (v/v); ammonium sulfate, 0.2% (w/v), $CaCO_3$, 0.5% (w/v); monopotassium phosphate anhydrous, 0.05% (w/v); lactose, 1.0% (w/v); primary dry yeast, 1.0% (w/v) in one liter of distilled water. Incubation was at 25° C. and 65% relative humidity on a rotary shaker with a 70 mm diameter amplitude at 220 rpm. After 48 hours of incubation, the production stage was initiated by transferring 2 mL of vegetative seed to 35 mL/500 mL flask of media with the following composition: $KH_2PO_4$, 0.05% (w/v); $K_2SO_4$, 0.5% (w/v); $(NH_4)_2SO_4$, 1.0% (w/v); lactose, 12.0% (w/v), pharmamedia, 2.75% (w/v); $CaCO_3$ (precipitated), 1.0% (w/v), lard oil, 1.0% (v/v) in one liter distilled water pH 6.6. Following autoclaving, but prior to inoculation, sterile 25% sodium adipate (pH 6.6) was added to give a final sodium adipate concentration of 2.5%. Incubation, following inoculation, was then continued under the same conditions as the seed stage for 5 to 7 days.

When mycelia were needed to generate protoplasts for transformation or as a source of DNA, the strain was grown in 50 mL/250 mL flask of complete media (CM) composed of: 50 mL of 20× Clutterbuck's salts (120 g $Na_2NO_3$, 10.4 g KCl, 10.4 g $MgSO_4$-7$H_2O$, 30.4 g $KH_2PO_4$), 2.0 mL Vogel's Trace Elements (0.3M citric acid, 0.2M $ZnSO_4$, 25 mM $Fe(NH_4)_2(SO_4)_2$-6$H_2O$, 10 mM $CuSO_4$, 3 mM $MnSO_4$, 8 mM boric acid, 2 mM $Na_2MoO_4$-2$H_2O$), 5 g tryptone, 5 g yeast extract, 10 g glucose, in one liter of distilled water. Incubation was at 25° C. on a rotary shaker at 220 rpm.

EXAMPLE 2

Isolation of Penicillium Genomic DNA and Total RNA

The vegetative mycelial growth from a 48 hour culture prepared as described above was collected by filtration through cheesecloth, frozen in liquid nitrogen and lyophilized overnight. The dried mycelia were ground with sand in a mortar and pestle and resuspended in 25 mL of 100 mM LiCl, 50 mM EDTA, 10 mM Tris pH 8.0, 4% SDS. After heating the suspension to 50°–55° C. in a 60° C. water bath, the mixture was extracted first with 1M Tris (pH8) saturated phenol, followed by Tris-saturated phenol:chloroform (1:1,v:v) and then chloroform. RNA was precipitated from the aqueous phase by the addition of an equal volume of cold 6M LiCl and then allowing the mixture to remain at −20° C. for two to three hours. After centrifugation at 12000×g for 20 minutes at 4° C., the supernatant was made 66% (v/v) ethanol and cooled to −20° C. for 15 minutes to precipitate the DNA. After centrifugation as described above, the DNA pellet was washed with 70% ethanol, dried and resuspended in TE Buffer (10 mM Tris-HCl, pH7.5, 1 mM EDTA). The DNA concentration was estimated by comparison to known DNA standards when stained with ethidium bromide in agarose gel electrophoresis.

Cultures of *Penicillium chrysogenum* as described above in Example 1 were grown for 96 hours in 35 mL of fermentation medium (fermentation conditions previously described), at 25° C. on a rotary shaker at 220 rpm. Mycelia were collected by filtration through a Whatman #1 filter under vacuum and washed with approximately 50 mL water. The mycelia were immediately scraped from the filter, resuspended in 5 mL of "breaking buffer" (50 mM Tris-HCl pH 7.4, 150 mM NaCl, 5 mM EDTA pH 8.0, 5% SDS), frozen in liquid nitrogen and lyophilized. After overnight lyophilization, 5 mL of water containing 0.1% DEPC and 5 mL of 1M Tris (pH 8) saturated phenol:chloroform:isoamyl alcohol (50:50:1) were added and the mixture was left to thaw at 37° C. for 20 minutes with shaking. The mixture was centrifuged at 12000×g for ten minutes at 4° C., and the aqueous layer was removed and re-extracted first with 1M Tris (pH 8) saturated phenol:chloroform:isoamyl alcohol (50:50:1), and second with 1M Tris (pH 8) saturated phenol, and third with chloroform. An equal volume of 6M LiCl was combined with the final aqueous layer, and the solution was left at −20° C. for a minimum of four hours. The total RNA was pelleted at 12000×g for 20 minutes at 4° C., the pellet dissolved in 0.3 mL TE buffer plus 0.03 mL of 3M sodium acetate, and 2.5 volumes of ethanol were added to reprecipitate the RNA. The final pellet was dissolved in 0.1 mL of TE buffer and the RNA concentration was determined spectrophotometrically using absorbance at 260 nm.

EXAMPLE 3

*Streptomyces clavuligerus* culture conditions

The *Streptomyces clavuligerus* strain used in these procedures was ATCC 27064. The strain was maintained on plates consisting of: yeast extract, 4 g; malt extract, 10 g; glucose, 4 g; agar, 20 g; in one liter of distilled water, pH 7.2. After 5 days of growth at 30° C., 2 mL of sterile water was added to the plates and the culture growth was scraped from the agar surface. The resulting suspension was transferred to a sterile screw-top tube containing glass beads. After macerating the culture growth by vortexing, the suspension was used to inoculate liquid cultures. The suspension was also used for permanent culture storage at −70° C. by adding glycerol to 15% final volume.

When mycelia were needed to generate protoplasts for transformation or for a source of DNA, the strains were grown in 200 mL/1 liter flask of YEME media composed of: yeast extract 3 g; peptone, 5 g: malt extract, 3 g; glucose, 10 g; sucrose, 340 g; MgCl$_2$-6H$_2$O, 1.02 g; glycine, 5 g; agar, 18 g; in one liter of distilled water. Incubation was at 28° C. on a rotary shaker at 220 rpm.

EXAMPLE 4

Isolation of Streptomyces Genomic DNA

The vegetative growth from a 48 hour culture prepared as described above was collected by centrifugation at 22100×g for 10 minutes. The cells were resuspended in 10 mL of TE buffer and 10 mg of lysozyme was added and the mixture was incubated at 30° C. for 15 minutes. One mL of 20% SDS was then added, immediately followed by 10 mL of TE (pH 8) saturated phenol and 1.5 mL of 5M NaCl and the mixture was inverted gently for 20 minutes. The phases were separated at 12000×g for 10 minute after which the aqueous layer was removed and transferred to a fresh tube. An equal volume of chloroform was added and the mixture was inverted gently for 10 minutes. The phases were separated again by centrifugation at 12000×g for 10 minutes and the aqueous layer removed and again transferred to a fresh tube. Two volumes of isopropanol were carefully added and the precipitated DNA was spooled and redissolved in a minimum volume of TE buffer. RNAse A was added to a final concentration of 20 mg/mL and the solution was incubated at 50° C. for one hour. Protease K was then added to a final concentration of 100 mg/mL, along with 100 mM NaCl and 0.4% SDS, and the mixture was incubated at 37° C. for one hour. The solution was extracted again with an equal volume of TE (pH 8) saturated phenol, followed by another chloroform extraction. The DNA from the final extraction was spooled after addition of two volumes of isopropanol and the concentration was determined spectrophotometrically using an absorbance reading at 260 nm.

EXAMPLE 5

Construction of a Gene Library and Isolation of a DNA Fragment Containing the *Streptomyces clavuligerus* Expandase Gene.

*Streptomyces clavuligerus* genomic DNA obtained from the procedure previously described was digested with the restriction enzymes Bam HI and Sal I. The digested DNA was electrophoresed on a 0.8% agarose gel and 1.8 to 2.2 kb sized fragments were eluted and ligated to pUC18 DNA which had been previously digested with Bam HI and Sal I. Dilutions of the ligation mixture were used to transform competent JM109 cells using electroporation (Gene Pulser, Bio-Rad, Richmond, Calif.). Preparation of the competent cells and electroporation conditions were both according to the manufacturer's recommendations. The transformation mix was plated onto LB plates containing 100 mg/mL ampicillin, and 75 mL of 2% X-Gal. Following overnight incubation at 37° C., recombinant colonies were identified by their colorless appearance due to inactivation of the plasmid vector beta-galactosidase gene activity. The colorless colonies were picked to a fresh LB plate containing 100 mg/mL ampicillin. After overnight growth at 37° C. the colonies were transferred to nitrocellulose and hybridized with a probe produced by polymerase chain reaction which corresponded to the published *Streptomyces clavuligerus* expandase gene sequence from bases 52–918 [Kovacevic et al. (1989) *J. Bacteriol.* 171: 754–760; and U.S. Pat. No. 5,070,020]. Labelling of the polymerase chain reaction product was accomplished by random-primer extension reaction with ($^{32}$P) dCTP and an Oligolabelling Kit, per the manufacturer's instructions (Pharmacia, Piscataway, N.J.). The hybridization reaction was performed in the presence of $10^6$ CPM of radiolabeled probe, 30% formamide, 5×SSC (0.15M NaCl, 0.015M sodium citrate pH7), 0.1% SDS, 5×Denhardt's (5 g ficoll, 5 g polyvinylpyrolidone, and 5 g BSA for 500 mL of 50×stock) and 100 mg/mL calf thymus DNA, at 37° C. overnight. Several transformants hybridized strongly to the probe. One colony was confirmed to contain a vector carrying the expandase gene by restriction enzyme analysis and this plasmid was designated pFTSO-1.

EXAMPLE 6

Isolation of Plasmid DNA

*E. coli* cultures containing the plasmid were grown in 500 mL LB broth (20 g/1 of LB Broth Base (Gibco, Paisley, Scotland), with 15 mg/mL tetracycline on a rotary shaker at 220 rpm for 12–16 hours at 37° C. The cells were pelleted by centrifugation at 4000×g for ten minutes at 4° C. The cell pellet was resuspended in 18 mL Glucose Buffer (50 mM glucose, 25 mM Tris pH8.0, 10 mM EDTA) and 2 mL of 40 mg/mL lysozyme (Sigma, St. Louis, Mo.) in glucose buffer was added, mixed, and the mixture was incubated at room temperature for 15 minutes. Forty mL of a freshly prepared solution of 0.2N NaOH, 1% SDS was added, and the mixture swirled gently and placed on ice for ten minutes. Thirty mL of 5M potassium acetate pH 4.8 were then added, mixed well, and the resultant mixture was placed on ice for an additional ten minutes. The cellular debris were pelleted by centrifugation at 400×g for ten minutes at 4° C. and the resulting supernatant was filtered through a cheesecloth filter. Isopropanol (0.6 volumes) was added to the clarified supernatant to precipitate the plasmid DNA, and the precipitate was formed during incubation at room temperature for 20 minutes. The plasmid DNA was pelleted at 4000×g for 20 minutes at 4° C. and then washed with 70% ethanol and dried briefly. The pellet was resuspended in 9 mL TE buffer, then 10 grams of CsCl and 0.387 mL of a 10 mg/mL ethidium bromide solution were added. This solution was centrifuged at 313,100×g for 24 hours. The resulting plasmid band in the cesium chloride gradient was visualized with ultraviolet light, isolated, and then the ethidium bromide was removed using water saturated butanol for extraction. The CsCl in the plasmid preparation was then removed by dialysis against TE buffer, and finally the DNA was concentrated using PEG (MW 8000). Concentration of DNA was determined spectrophotometrically using an absorbance reading at 260 nm.

EXAMPLE 7

Construction of the Penicillium Transformation Vector pPenFTSO

A Penicillium transformation vector was constructed with a phleomycin resistant gene as a dominate selectable marker. This was accomplished first by isolating a 660 bp fragment, containing the phleomycin resistance gene (a phleomycin binding protein gene from *Streptoalloteichus hindustanus*) and also coupled to a yeast cytochrome C1 terminator, from a Bam HI/Bgl II digest of plasmid pUT713 (CAYLA, Toulouse Cedex, France) by electrophoresis on and elution from agarose gels. The isolated fragment was ligated into the Bam HI site of vector pSELECT® 1 (Promega Corporation) and the orientation of the gene was determined by restriction enzyme analysis. Next, a 550 bp Pst I fragment, containing the lambda cos site was inserted which enables the vector to be used for cosmid formation when appropriate size inserts are included. Then, a 1.5 kb Nco I/Bam HI fragment, containing the promoter region of the *Penicillium chrysogenum* isopenicillin N synthetase (IPNS) gene, was isolated (by electrophoresis on and elution from agarose gels) from an Nco I/Bam HI digest of a genomic clone containing the IPNS gene. The isolated IPNS-promoter fragment was ligated into the Bam HI/Nco I digested vector. The Nco I site is at the ATG start codon of the phleomycin resistance gene. This vector is designated pUTZ-2.

The 1.645 kb fragment containing the *Streptomyces clavuligerus* expandase gene was purified from a Bam HI and Sal I digest of the pFTSO-1 (vector previously described) by electrophoresis on and elution from a 0.8% agarose gel. The isolated fragment was ligated into vector pSELECT (Promega Corporation) also digested with Bam HI and Sal I. This vector was designated pFTSO-8. A novel Nco I site was created at the ATG start codon of the expandase gene by site-directed mutagenesis of pFTSO-8 using the Altered Sites® in vitro Mutagenesis System (Promega Corporation). Mutagenesis was performed per the manufacturer's instructions. An oligonucleotide was constructed to complement the coding sequence of the DNA region at the ATG start codon from the published sequence of the Streptomyces expandase gene (Kovacevic et al, (1990) Journal of Bacteriology, 171, p. 3952-3958). The oligonucleotide was synthesized by cyanoethyl phosphoramidite chemistry (Pharmacia Gene Assembler instrumentation), and the oligo sequence was as follows:

SEQ ID NO:8
3' CGAGAGGATCAGTGAGAGTCCATGGACACGACGG 5'.

The mutagenesis was confirmed by restriction enzyme analysis. Next, a 1.2 kb Nco I fragment, containing the promoter region of the *Penicillium chrysogenum* isopenicillin N synthetase gene, was isolated (by electrophoresis on and elution from agarose gels) from an Nco I digest of a genomic clone containing the IPNS gene. The IPNS-promoter region was ligated into the pFTSO-8 vector at the novel Nco I site created by the mutagenesis at the ATG start codon of the expandase gene. Orientation of the promoter to the expandase gene was established by restriction enzyme analysis. This IPNS-promoter: expandase gene cassette was then removed as a Bam HI/Sal I fragment into the Bam HI/Sal I cut Penicillium transformation vector pUTZ-2 described above. The final construction was designated pPenFTSO.

EXAMPLE 8

Cloning of the Penicillium β-Tubulin Promoter

The Penicillium β-tubulin gene were cloned from a Penicillium lambda genomic library using the *Aspergillus niger* β-tubulin gene as a hybridization probe. Sequencing of this clone and comparison to the known amino acid sequence of the β-tubulin gene of *Aspergillus niger* identified a region of 91% homology beginning with the ATG initiation codon. Sequences comprising a functional promoter were isolated between the initiation codon and a Bam HI site 1.4 kb upstream.

Construction of the Transformation Vector Carrying the Penicillium β-Tubulin Promoter A 2.0 kb Xba I/Hind III fragment containing the Penicillium β-tubulin promoter was ligated into vector pSELECT (Promega Corporation) also digested with XbaI/Hind III. A novel Nco I site was created at the ATG start codon by site-directed mutagenesis using the Altered Sites in vitro Mutagenesis System (Promega Corporation). Mutagenesis was performed per the manufacturer's instructions. An oligonucleotide was constructed complementary to the ATG start site region, but which incorporated several changes to create an Nco I site, and used for mutagenesis. The oligonucleotide was synthesized by cyanoethyl phosphoramidite chemistry (Pharmacia Gene Assembler instrumentation) and the oligo sequence was as follows:

Seq. ID No:9
5' ATCTCTTTTCTAATACCTTCACCATGGGTGAGATTGTACGTGATCCC 3'.

The mutagenesis was confirmed by restriction enzyme analysis. Next, a 1.4 kb Bam HI/Nco I fragment containing the Penicillium β-tubulin promoter was ligated to an engineered Nco I site at the ATG of the Streptomyces expandase gene in the Bam HI/Nco I digested vector pFTSO-8 (vector previously described in Example 7). This vector was designated btFTSO-8. The 1.4 kb Bam HI/Nco I fragment containing the β-tubulin promoter was also ligated into a Bam HI/Nco I digested vector pUTZ-2 (vector previously described in Example 7). This ligation positioned the β-tubulin promoter directly in front of the phleomycin resistant gene. This vector was designated pCI-6. Next, a 2.4 kb Bam HI/Hind III fragment from vector btFTSO-8 which contained the β-tubulin promoter expandase gene cassette was ligated to a Bam HI/Hind III digested vector pCI-6 to yield the final Penicillium transformation vector in which the Streptomyces expandase gene and phleomycin resistance marker were expressed from the β-tubulin promoter. This vector was designated pTS-2.

EXAMPLE 9

Cloning of the Penicillium (GAP) Promoter

The Penicillium glyceraldehyde-3-phosphate dehydrogenase (GAP) gene was cloned from a Penicillium lambda genomic library using the GAP gene from *Aspergillus niger* as a hybridization probe. Four potential positives were further probed with a PCR product generated from primers for the 5' region of the Cephalosporin GAP gene (Kimura, H. et al., (1991), *J. Ferm. and Bioeng.*, 71, 145–150). The oligonucleotides used for the primers of the polymerase chain reaction (PCR) were synthesized by cyanoethyl phosphoramidite chemistry (Pharmacia Gene Assembler instrumentation) and the oligo sequences are as follows:

Seq. ID No:10
5' CGCGGATCCCGGCATCAACGGCTTCGGTCGTAT 3'
Seq. ID No:11
5' CGCGGATCCGGGCACGCGCATGGACATGCCAGTG 3'.

One of the four putative positives cross hybridized to the PCR product. A four kb Bam HI fragment from this genomic clone was ligated into Bam HI digested vector pSELECT (Promega Corporation) for sequencing. This vector was designated pTS-0. Sequencing of this fragment identified the ATG initiator codon by comparison to the known sequence of the Cephalosporin GAP gene.

Construction of the Transformation Vector Carrying the Penicillium GAP Promoter

For engineering the Penicillium GAP promoter with the Streptomyces expandase gene a novel Nco I site was created at the ATG of the Penicillium GAP gene by in vitro site-directed mutagenesis using vector pTS-0. Mutagenesis was performed per the manufacturer's instructions. An oligonucleotide was constructed to be complementary to the coding sequence of the DNA region at the ATG start codon of the GAP gene, but incorporating base changes to create an Nco I site. The oligonucleotide was synthesized by cyanoethyl phosphoramidite chemistry (Pharmacia Gene Assembler instrumentation), and the oligo sequence was as follows:

Seq. ID No:12
5' CAGTAAACGCAACCATGGTTGTCCAG 3'.

Mutagenesis was confirmed by restriction enzyme analysis. Next, a 1.9 kb NcoI/Bam HI fragment from pTS-0 which contained the GAP promoter was ligated to NcoI/Bam HI digested vector pFTSO-8 (vector previously described in Example 7) for positioning of the GAP promoter with the Streptomyces expandase gene. This vector was designated pTS-0-1. Next, a 3.0 kb Bam HI/Hind III fragment from vector pTS-0-1 which contained the GAP promoter: expandase cassette was ligated to Bam HI/HInd III digested vector pCI-6 (vector previously described in Example 8) to yield the final Penicillium transformation vector pSD-1 in which the Streptomyces expandase gene was expressed from the GAP promoter.

EXAMPLE 10

Transformation of *Penicillium chrysogenum*

Protoplasts from the *Penicillium chrysogenum* strain described above were generated by inoculating 50 mL of CM broth with $1 \times 10^7$ spores for 67 hours at 25° C. on a rotary shaker at 220 rpm. The mycelia were collected by filtration onto cheesecloth filters, transferred to 500 mL flasks and resuspended in 25 mL KMP (0.7M KCl, 0.8M mannitol, 0.02M $KPO_4$ pH6.3), containing 100 mg Novozyme 234 (Novo BioLabs, Bagsvaerd, Denmark) and allowed to incubate at 30° C. at 100 rpm. The spheroplasts were separated by filtration through cheesecloth/glasswool filters and pelleted by centrifugation at $350 \times g$ for 10 minutes. The spheroplasts were then washed three times with 10 mL of KMP buffer, and then resuspended in KMPC (KMP with 50 mM $CaCl_2$) to a concentration of $5 \times 10^7$ cells/mL and left at room temperature for 20 minutes. For transformation of the Penicillium, 200 ml of the spheroplast suspension was added to DNA (5 mg vector DNA in 6.2 ml of KMPC with 5 mg/mL heparin) along with 50 ml of PPC (40% PEG MW 3500, 20 mM $KPO_4$, pH 6.3, 5% $CaCl_2$ was added just before use) and the transformation mix was incubated on ice for 30 minutes. One mL of freshly prepared PPC was added and the mixture was transferred to 50 mL of molten (50° C.) regeneration agar (CM plus 1.3M mannitol and 3% agar). The transformation mixture was then distributed between 5 petri dishes. After regeneration for 24 hours at 25° C. the plates were then overlayed with OL (1% peptone in 1% agar) containing 100 mg/50 mL OL of phleomycin. The amount of overlay was equal to the amount of regeneration agar. The plates were incubated at 25° C. for 7–14 days and observed for generation of transformant colonies.

EXAMPLE 11

HPLC Assays of Adipoyl-6-APA and Adipoyl-7-ADCA Fermentation Products

High performance liquid chromatography (HPLC) was used to assay the adipoyl-6-APA production in the untransformed *P. chrysogenum* strain which was used, and the adipoyl-7-ADCA production in the transformed *P. chrysogenum* strain which was used. The analysis was done on Waters system with 625 solvent delivery system, 490E variable wavelength detector set at 220 nm and 254 nm, 825 Maxima data system, and a Novo-C18 column as the stationary phase. The mobile phase (at a 1 mL/min. flow rate) consisted of a 5 minute isocratic 2% methanol/98% 0.010M $KH_2PO_4$, pH 7.0, and a 15 minute, 2 to 40% linear gradient of methanol/0.010M $KH_2PO_4$, pH 7.0. Quantitation of the adipoyl-6-APA was determined using a standard curve of the standard penicillin N at 220 nm, and the quantitation of the adipoyl-7-ADCA was determined using a standard curve of the standard deacetoxycephalosporin C at 254 nm.

Assays for susceptibilities of the adipoyl-6-APA and adipoyl-7-ADCA to penicillinase treatments were done by adding 1 unit/mL of penicillinase I or penicillinase III to filtrates and incubating at room temperature for 10–30 minutes. These samples were run under identical HPLC conditions as described above.

UV spectra analysis of the adipoyl-6-APA and adipoyl-7-ADCA products was done using a Waters system with 510 solvent delivery system, 990 photodiode array detector, 990 data system, and a Novo-C18 column as the stationary phase. The mobile phase used was identical to conditions described above.

Large scale isolation of the adipoyl-7-ADCA product from whole fermentation broth was done using a Waters system with 510 solvent delivery system, 990 photodiode array detector, 990 data system, and a μBondapak C18 preparative column as the stationary phase. The mobile phase (at a 5 mL/min flow rate) consisted of an isocratic 0.010M $KH_2PO_4$ pH 7.0 for 35 minutes. The absorption peak corresponding to the retention time of the adipoyl-7-ADCA product was collected using a fraction collector.

EXAMPLE 12

Bioactivity Assays

An agar diffusion bioassay was used to determine antibiotic activity of the HPLC isolated adipoyl-6-APA and the adipoyl-7-ADCA fermentation products. Twenty μL of isolated product was applied to 5 mm discs on an LB agar plate (20 g/L of LB Broth Base with 3% agar (Gibco, Paisley, Scotland) seeded with *Bacillus subtilus* ATCC 33677, or *E. coli* Super Sensitive strain (supplied by Prof. Arnold L. Demain, MIT). *Bacillus subtilus* was used as the indicator strain to assay the adipoyl-6-APA product and the *E. coli* Super Sensitive strain was used as the indicator strain to assay the adipoyl-7-ADCA product. After 15 hours of incubation at 37° C. a halo of inhibited growth of the indicator bacteria around the disk indicated the products showed bioactivity. The controls in this experiment included deacetoxycephalosporin C, cephalosporin C, penicillin V, and agar containing penicillinase or no penicillinase as a control for confirmation of β-lactam structures.

EXAMPLE 13

RAEV Enzyme Assays

Purified adipoyl-7-ADCA product from whole fermentation broth was used as a substrate to determine the specific activity of the RAEV enzyme (commercially available from RAEV Corp.). The reaction mix contained 10 mM substrate, 1 mg RAEV enzyme, 5% glycerol, in 0.16M $KH_2PO_4$ in a total volume of 50 ml, and was incubated at 37° C. Five ml aliquots were taken at time points 0, 1, 3, 5, 10, 20, and 30 minutes, diluted with 35 ml of 0.010M $KH_2PO_4$ pH 3.5, and frozen at −70° C. before analysis by HPLC under conditions previously described.

Activity of the RAEV enzyme against a colorimetric adipoyl-P-aminobenzoic acid substrate was assayed using 5 mM substrate, 8.25 mg RAEV enzyme, 10% glycerol, in 0.065M $KH_2PO_4$ pH 7.0, in a total volume of 50 ml for 30 minutes at 37° C. The reaction was carried out in a 96 well microtiter dish. Fifty ml of a 1/100 dilution of 1M $NaNO_2$ in 0.25M acetic acid was added to terminate the reaction and the reaction was left at room temperature for 3 minutes. One hundred ml of a 1/100 dilution of 10 mg/mL 4-amino-5-hydroxy-2,7-naphthalene-disulfonic acid, monosodium salt hydrate in $H_2O$ into 0.5M $NaHCO_3$ was added and the color development was monitored immediately at 515 nm using a EL 312 Bio-kinetics Plate Reader (BioTek Instruments).

EXAMPLE 14

HPLC Assay of RAEV Enzyme Reaction Product

All of the RAEV enzyme (commercially available from RAEV Corp.) assays using the adipoyl-7-ADCA substrate which were monitored by HPLC were done using a Waters system with 625 solvent delivery system, 490E variable wavelength detector set at 203 nm and 254 nm, 825 Maxima data system, and a Novo-C18 column as the stationary phase. The mobile phase (at a 1 mL/min flow rate) consisted of a 5 minute isocratic 2% methanol/98% 0.010M $KH_2PO_4$, pH 3.5, and a 15 minute, 2–40% linear gradient of methanol/0.010M $KH_2PO_4$ pH 3.5. The standard 7-ADCA was used to monitor retention time of the reaction product. Quantitation of the reaction product was calculated using a standard curve of the standard 7-ADCA at 254 nm.

EXAMPLE 15

13C-NMR Analysis of the Adipoyl-7-ADCA Fermentation Product

The 13C-NMR (broad band proton-decoupled) spectra was obtained at 75.4 MHz (7.1T) on an 1BM-AF-350 spectrometer in the Fourier Transform mode. The samples consisted of 50 mg of adipoyl-7-ADCA product from fermentation broth in 0.5 ml D20 (99.8% D, Aldrich), or 0.5 mL DMSO-$d_6$ (99.0% D, Aldrich), in 5 mm tubes at 350° k. The NMR data confirmed the product designation as adipoyl-7-ADCA.

EXAMPLE 16

Assessment of Alternative Adipoyl Acylase Enzymes

In addition to the studies using the RAEV enzyme, the removal of the adipoyl side-chain from adipoyl-7-ADCA (and other adipoyl-compounds) was demonstrated with enzymes produced from a variety of microbial sources. In an initial study the Pseudomonas sp. strains SE-83 and SE-495 (deposited with the Fermentation Research Institute under the accession numbers FERM BP-817 and FERM BP-818 respectively) and the Pseudomonas strain SY-77-1 (deposited with the Northern Regional Research Laboratory under the accession number NNRL B-8070) were grown for 72 hours in a medium containing HyCase SF, 2.0% (w/v); monosodium glutamate, 0.5% (w/v); yeast extract, 0.5% (w/v); corn steep powder, 0.2% (w/v); cotton seed oil, 0.5% (w/v) and glutaric acid, 0.1% (w/v).

Cells were harvested by centrifugation and washed with 50 mM phosphate buffer, pH 8.0; they were then resuspended in buffer and the outer membranes made permeable by the addition of a small volume of chloroform. Aliquots of cell suspension were then mixed with adipoyl-para-nitroaniline (ad-PNA) and incubated at 30° C. for periods of 2 to 18 hours. Following incubation, the mixtures were acidified by the addition of 10% (v/v) acetic acid. Liberated p-nitroaniline was then detected by colorimetric means following its conversion to a diazo compound utilizing the reagents supplied in kit-form by Sigma Chemical Company for the assay of gamma-glutamyl-transferase (Sigma product number 545-A). The relative activities of the three strains were 100%, 85.5% and 48% for SE-495, SE-83 and SY-77-1 respectively. Using methods similar to those described for the RAEV enzyme above, activity of the SE-83 and SE-495 enzymes on adipoyl-7-ADCA was also demonstrated. The production of beta-lactamase by SY-77-1 prevented the demonstration of deacylating activity by this strain on adipoyl-7-ADCA.

By similar means adipoyl-acylase production was also demonstrated for two fungal strains (Alternaria sp. MA-133, ATCC No. 20492 and Aspergillus sp. MA-13, ATCC No. 20491; ref. U.S. Pat. No. 4,141,790 to Meiji Seika Kaisha Ltd.) and three additional bacterial strains (a Brevibacterium, ATCC No. 14,649; and Achromobacterium, ATCC No. 14,648 and a Flavobacterium, ATCC No. 14,650) which were described as cephalosporin C acylase producers in U.S. Pat. No. 3,239,394 to Merck & Co., Inc.

---

What is claimed is:

1. A bioprocess for preparing 7-aminodesacetoxy cephalosporanic acid (7-ADCA) comprising the steps of 1) maintaining in a culture medium capable of sustaining its growth, a strain of *Penicillium chrysogenum* which produces isopenicillin N and adding to said culture medium an adipate feedstock comprising adipic acid, or one or more of its salts and esters which are capable of being assimilated and utilized by said strain of *Penicillium chrysogenum* to produce adipoyl-6-amino penicillanic acid (adipoyl-6-APA), whereby said adipoyl-6-APA is produced; wherein said strain of *Penicillium chrysogenum* has been transformed by DNA encoding *Streptomyces clavuligerus* expandase enzyme capable of accepting said adipoyl-6-APA as a substrate, whereupon as a result of its expression, said adipoyl-6-APA produced by said strain is also thereafter in situ ring-expanded to form adipoyl-7-ADCA; and 2) contacting said adipoyl-7-ADCA with an adipoyl acylase whereby the adipoyl side chain is removed and the 7-ADCA product is formed; and said product is then isolated.

2. A bioprocess according to claim 1 wherein the adipate feedstock is disodium adipate.

3. A bioprocess according to claim 1 wherein the DNA encoding expandase enzyme is derived from *Streptomyces clavuligerus* ATCC 27064.

4. A bioprocess according to claim 1 wherein the adipoyl acylase is derived from a Pseudomonas species.

5. A method of producing adipoyl-7-ADCA in vivo comprising culturing a recombinant *Penicillium chrysogenum* host cell designated PC100, ATCC 74182 in the presence of adipic acid, or salts and esters thereof, wherein said host cell is expressing recombinant expandase enzyme.

6. An in vivo method for the in situ production of adipoyl-7-ADCA comprising the steps:

(a) producing adipoyl-6-APA by adding adipic acid or the salts and esters thereof to a culture of *Penicil-* lium chrysogenum strain PC100, ATCC 74182 in a suitable culture medium; and (b) converting adipoyl-6-APA to adipoyl-7-ADCA in vivo.

7. A method for the production of 7-ADCA comprising the steps:

(a) producing adipoyl-6-APA in vivo by adding adipic acid or the salts and esters thereof to a culture of *Penicillium chrysogenum* strain PC100, ATCC 74182 in a suitable medium;

(b) converting adipoyl-6-APA to adipoyl-7-ADCA in vivo; and (c) contacting the adipoyl-7-ADCA with an adipoyl acylase whereby the adipoyl side chain is removed and the 7-ADCA product is formed.

* * * * *